United States Patent [19]

Gulyás et al.

[11] Patent Number: 4,647,553

[45] Date of Patent: Mar. 3, 1987

[54] GONADOLIBERIN DERIVATIVES AND PROCESS FOR THE PREPARATION THEREOF

[75] Inventors: Tamás Gulyás, Szekszárd, Szeksárd; Anikó Horváth, Budapest; György Kéri, Budapest; Károly Nikolics, Budapest; Balázs Szöke, Budapest; István Teplán, Budapest, all of Hungary

[73] Assignee: Innovacios Alap Kozponti Valto Es Hitelbank RT., Budapest, Hungary

[21] Appl. No.: 684,065

[22] Filed: Dec. 20, 1984

[30] Foreign Application Priority Data

Dec. 23, 1983 [HU] Hungary ................ 4458/83

[51] Int. Cl.⁴ .................... A61K 37/43; C07K 7/20
[52] U.S. Cl. ............................ 514/15; 530/313; 514/800
[58] Field of Search ............ 514/800, 15; 530/313

[56] References Cited

U.S. PATENT DOCUMENTS

| | | | |
|---|---|---|---|
| 4,008,209 | 2/1977 | Fujino et al. | 514/800 |
| 4,083,967 | 4/1978 | Beddell et al. | 514/800 |
| 4,118,483 | 10/1978 | Konig et al. | 514/800 |
| 4,213,895 | 7/1980 | Immer et al. | 514/800 |
| 4,410,514 | 10/1983 | Vale, Jr. et al. | 514/800 |
| 4,530,920 | 7/1985 | Nestor et al. | 514/800 |

*Primary Examiner*—Delbert R. Phillips
*Attorney, Agent, or Firm*—Keil & Weinkauf

[57] ABSTRACT

The invention relates to gonadoliberin derivatives of the general formula (I)

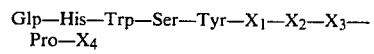

Glp—His—Trp—Ser—Tyr—$X_1$—$X_2$—$X_3$—Pro—$X_4$ wherein $X_1$ is a glycyl group or a D-isomer of any natural or synthetic amino acid group, $X_2$ represents an L-amino acid group having 1 to 4 carbon atoms in the side chain, L-phenyl-alanyl or L-tryptophyl group, $X_3$ represents an L-amino acid group having a $C_{1-4}$ alkyl or $C_{2-4}$ alkanoyl-amide side chain, and $X_4$ is a glycine amide or a $C_{1-4}$ alkyl amide group, with the proviso that if $X_1$ stands for a group other than glycyl and $X_2$ is a tryptophyl group then $X_3$ may not be leucyl, and the addition salts formed with therapeutically useable acids and complexes thereof. Furthermore the invention relates to a process for preparing these compounds.

The new gonadoliberin derivatives can be effectively used for the reproduction process of fish, birds and mammals.

4 Claims, No Drawings

GONADOLIBERIN DERIVATIVES AND PROCESS FOR THE PREPARATION THEREOF

The invention relates to new gonadoliberin derivatives and a process for preparing same.

More specifically, the invention relates to new gonadoliberin derivatives having the general formula (I)

Glp—His—Trp—Ser—Tyr—$X_1$—$X_2$—$X_3$—Pro—$X_4$     (I)

and the addition salts formed with therapeutically usable acids and complexes thereof as well as to pharmaceutical compositions containing them. In the general formula (I)

$X_1$ is a glycyl group or a D-isomer of any natural or synthetic amino acid group, $X_2$ represents an L-amino acid group having 1 to 4 carbon atoms in the side chain, L-phenyl-alanyl or L-tryptophyl group, $X_3$ represents an L-amino acid group having a $C_{1-4}$ alkyl or $C_{2-4}$ alkanoyl-amide side chain, and $X_4$ is a glycyl amide or a $C_{1-4}$ alkyl-amide group, with the proviso that if $X_1$ stands for a group other than glycyl and $X_2$ is a tryptophyl group then $X_3$ may not be leucyl.

The abbreviations used in the formula are identical with the nomenclature accepted in peptide chemistry which is disclosed e.g. in J. Biol. Chem. [241, 527 /1966/].

It is a general property of the gonadoliberin (other names known in the literature: gonadotrop releasing hormone, GnRH, luteinizing and folliculus stimulating hormone, LH/FSH) and its known derivatives that they are able to release the luteinizing hormone (LH) and the folliculus stimulating hormone (FSH).

From the early eighties it has become known from the literature that the gonadoliberin of certain fishes and birds differs structurally from the mammalian one [J. A. King and R. P. Millar, J. Biol. Chem. 257, 10722–28 (1982); South-African Journal of Science 78, 124 (1982); N. Sherwood et al., Proc. Natl. Acad. Sci. 80, 2794–2798 (1983)]. These differences are to be found in the amino acids of positions 7 and/or 8.

It is also known from the literature that those derivatives of gonadoliberin which contain in position 6 certain D-amino acids, instead of the glycine, show increased biological activity compared to the native gonadoliberin (J. Sandow et al., Control of Ovulation, Butterworth, London, 1978, pp. 49–70).

It is known further that the substitution of the glycine amide moiety in position 10 by amide groups with aliphatic carbon chain [M. Fujino et al., J. Med. Chem. 16, 1144–1147 (1973)] raises the biological activity even to a higher level.

The present invention aims at preparing new gonadoliberin derivatives which are effectively usable for the reproduction process of fishes, birds and mammals.

Besides, the invention provides further derivatives having increased biological activity in relation to the native ones.

The invention is based on the recognition that the change of amino acids in positions 7 and 8 in the gonadoliberin molecule to other amino acids and certain combinations of these changes, respectively, result in gonadoliberin analogues suitable for reproduction of fishes, birds and mammals.

Furthermore, the invention is based on the recognition that the effectiveness of gonadoliberin derivatives prepared by changing the amino acids in positions 7 and 8 can be increased by inserting certain D-amino acids into position 6 and alkyl-amide groups into position 10, instead of glycine and glycine amide, respectively.

The nonapeptide-$C_{1-4}$-alkyl-amides and decapeptide amides of the general formula (I)

Glp—His—Trp—Ser—Tyr—$X_1$—$X_2$—$X_3$—Pro—$X_4$     (I)

wherein the meaning of $X_1$, $X_2$, $X_3$ and $X_4$ is the same as above, and the salts and complexes thereof can be prepared according to the invention as follows:

(a) using the method of solid-phase peptide synthesis, the appropriately protected amino acids are coupled in the required sequence to a solid polymer support with the aid of carbodiimide or active ester and, in a given case, the ready peptide is split off from the support by acidolysis or aminolysis and, if desired, the protecting groups of the amino acids are removed from the peptide simultaneously, before or after splitting off the peptide from the polymer support, or (b) the required end product is built up from the suitable protected amino acids by using an adequate combination of fragment condensation and stepwise synthesis, depending on the chemical character of the variable amino acid components.

It is advantageous to use benzhydrylamine or Boc-proline resin as solid support.

It is suitable to eliminate the protected peptide from the support by treatment with hydrogen fluoride and-/or by ethyl-ammonolysis.

According to the variant (b) it is preferable to prepare the new nona- or decapeptide derivatives by condensing a pentapeptide azide of the formula (II)

Glp—His—Trp—Ser—Tyr—$N_3$     (II)

with a tetra- or pentapeptide of the general formula (III), $X_1$—$X_2$—$X_3$—Pro—$X_4$     (III)

or by condensing a hexapeptide azide of the general formula (IV)

Glp—His—Trp—Ser—Tyr—$X_1$—$N_3$     (IV)

with a tri- or tetrapeptide of the general formula (V)

$X_2$—$X_3$—Pro—$X_4$,     (V)

or by condensing a heptapeptide azide of the general formula (VI)

Glp—His—Trp—Ser—Tyr—$X_1$—$X_2$—$N_3$     (VI)

with a di- or tripeptide of the general formula (VII)

$X_3$—Pro—$X_4$,     (VII)

wherein $X_1$, $X_2$, $X_3$ and $X_4$ are as defined above.

If desired, the nona- or decapeptide amide obtained can be converted to an acid salt by reacting it with a pharmaceutically suitable acid or, if desired, the free base can be liberated from an acid addition salt with a base and, if desired, a nona- or decapeptide-amide obtained can be converted to a metal complex.

Furthermore, the invention relates also to pharmaceutical compositions containing as active components compounds of the general formula (I) and their salts and complexes.

The pharmaceutical compositions are generally prepared by admixing at least one compound of the formula (I) or a pharmaceutically acceptable salt or complex thereof with carriers and/or additives conventionally used in the preparation of pharmaceutical compositions and formulating the compositions obtained for example as tablets, dragées, capsules, suppositories, injectable solutions, nasal sprays, etc.

The gonadoliberin derivatives of the formula (I) can effectively be used in fishes, birds and mammals when administered intramuscularly or subcutaneously in a dose of 0.1 µg to 5 mg.

The main advantage of the compounds according to the invention is that the new gonadoliberin derivatives of the general formula (I) contain amino acid combinations in positions 7 and 8 which are characteristic of fishes and birds, whereby they can be preferably used for the reproduction process of these animal species, too.

Further details of the invention are illustrated by the aid of the following non-limiting Examples.

In the Examples 1 to 5 the compounds are synthetized by the solid-phase technique [Merrifield, R. B., J. Am. Chem. Soc. 85, 2149–2151 (1953)], using chloromethylated polystyrene divinylbenzene resin in the case of peptide alkyl-amides, or benzhydrylamine resin in the case of peptide amides. The individual amino acids are coupled to the resin as their N-α-tert-butyloxycarbonyl (Boc) derivatives, using dicyclohexylcarbodiimide (DCC), N,N'-diisopropylcarbodiimide (DIC) or active ester method. The reactive side-chain groups of the amino acid are protected, if desired, with appropriate protecting groups.

The completeness of the coupling reaction is measured by ninhydrin test [Kaiser, E., Colescott, R. L., Bossinger, C. D., and Cook, P. I., Anal. Biochem. 34, 595–598 (1970)]. If the test is positive, the coupling is repeated. The duration of the coupling changes between 1 and 16 hours, depending on the amino acid.

Deprotection of the peptide as well as cleavage of the peptide from the resin are preferably carried out in one step, with liquid hydrofluoric acid (HF) [Sakakibara, S., Shimonishi, Y., Kishida, Y., Okada, M., and Sugikara, H., Bull. Soc. Japan 40, 2164–2167 (1967)]. When $N^{im}$-dinitrophenyl (DNP) protecting group is used, it is removed from the side chain of histidin before the HF cleavage. The protected peptide resin is stirred in dimethylformamide (DMF) containing a few drops of propylamine. After removing the solvent, the peptide resin is treated with hydrogen fluoride in the usual manner. Where a compound of peptide alkylamide type is to be prepared, the peptide is separated from the resin by alkyl-ammonolysis followed by hydrogenolysis and/or acidolysis, depending on the nature of the protecting groups.

The crude product gained after the HF cleavage is subjected to gel filtration on a column packed with Sephadex G-25, using an acetic acid solution as eluent. Further purification is carried out using preparative high-performance liquid chromatography (HPLC) and/or silica gel chromatography. The purity of the peptides is tested by amino acid analysis and by thin layer chromatography (TLC). The TLC $R_f$-values are determined on Kieselgel (DC, Alufolien, Merck) plates using the following solvent mixtures:

1. Ethyl acetate/pyridine/acetic acid/water 30:20:6:11
2. Ethyl acetate/pyridine/acetic acid/water 60:20:6:11
3. Ethyl acetate/pyridine/acetic acid/water 120:20:6:11
4. Ethyl acetate/pyridine/acetic acid/water 240:20:6:11
5. n-Butanol/acetic acid/water/ethyl acetate 1:1:1:1
6. n-Butanol/acetic acid/water 4:1:1
7. i-Propanol/1M acetic acid 2:1
8. Ethyl acetate/pyridine/acetic acid/water 5:5:1:3
9. n-Butanol/acetic acid/ammonia (1 cc $NH_3$:4$H_2O$)/water 6:1:1:2
10. Methyl-ethyl-ketone/acetic acid/water 120:15:20

EXAMPLE 1

Preparation of D—Phe$^6$, Gln$^8$-gonadoliberin M: 1243

(a) Synthesis 1.25 g (1 mmole) of benzhydrylamine resin.HCl [0.8 meq/g] (Pierce) are swollen in $CH_2Cl_2$ for two hours, then the next schedule is used for coupling the amino acid residues:

| Step | Reagents and operations | Mix times (min) |
|---|---|---|
| 1 | $CH_2Cl_2$, wash 3 times | 1 |
| 2 | 33 percent trifluoro acetic acid (TFA) in $CH_2Cl_2$ | 1 |
| 3 | 33 percent TFA in $CH_2Cl_2$ | 25 |
| 4 | $CH_2Cl_2$, wash 3 times | 1 |
| 5 | $CHCl_3$, wash 2 times | 1 |
| 6 | 10 percent triethyl-amine (TEA) in $CHCl_3$, 2 times | 2 |
| 7 | $CHCl_3$, wash 2 times | 1 |
| 8 | Ethanol, wash 2 times | 1 |
| 9 | $CH_2Cl_2$, wash 2 times | 1 |
| 10 | Boc—amino acid (3 mmoles) in $CH_2Cl_2$ and, if desired, DMF, plus DIC or DCC (3 mmoles) in $CH_2Cl_2$* | 60 - variable |
| 11 | $CH_2Cl_2$, wash 2 times | 1 |
| 12 | Ethanol, wash 2 times | 1 |

*Gln is coupled as its Boc—Gln—ONP (p-nitrophenyl) derivative by active ester method; in the case of Glp the α-amino group is not protected After each cycle (after step 12) an aliquot is taken off for ninhydrin test; if the test is negative, the next cycle is started at step one, and if it is positive, another recoupling (steps 5–12) is introduced.

At the end of the synthesis 2.28 g of Glp—His(Tos)—Trp—Ser(OBzl)—Tyr(OBzl)—D—Phe—Leu—Gln—Pro—Gly—peptide resin are gained. ΔW: 1.05 g (66%) ($M_{protected\ peptide}$: 1577)

(b) HF cleavage

The protected peptide (2.28 g) is treated with redistilled HF (30 ml) in the presence of anisole (3 ml) and dithiothreitol (100 mg) for 60 min at 0° C. The HF is eliminated in anhydrous nitrogen gas stream, the resin is then suspended in absolute ether and filtered. The solid residue is washed with 50% acetic acid, then the solution is evaporated in vacuo at 37° C. The evaporated material is directly subjected to gel filtration (see step (c) below).

(c) Gel filtration

The crude peptide [obtained in step (b)] is purified on a column of Sephadex G-25 (2.5×100 cm) in 50% acetic acid at a flow rate of 15 ml/h. The separation is monitored by UV absorption at 280 nm and by TLC. Fractions (300–350 ml) are collected and lyophilized. Yield: 690 mg (55%).

(d) Preparative HPLC

Further purification is carried out using a reversed-phase $C_{18}$-bonded silica gel LRP-1 (13–24 μm) (Whatman) preparative HPLC column (2.5×45 cm) which is equilibrated with a solution of 25% methanol in 30% acetic acid. After equilibration, 230 mg of gel-filtered material are loaded on the column. The elution is carried out with a linear gradient system of methanol-—30% acetic acid (25–40% methanol) at a flow rate of 2 ml/min and a pressure of $3.5 \times 10^5$ Pa. The contents of the fractions are measured at 280 nm and monitored by TLC. Collection and lyophilization of the product yield 133 mg of D—Phe$^6$, Gln$^8$—GnRH. Absolute amount should be multiplied by 3 for normalization to 690 mg of gel-filtered material (399 mg, 32%).

$R_f^1 = 0.76$;    $R_f^5 = 0.68$;    $R_f^6 = 0.33$;    $R_f^7 = 0.93$; $R_f^8 = 0.83$.

Amino acid analysis: Ser 0.93, Glu 1.96, Pro 0.95, Gly 1.02, Leu 1.00, Tyr 1.01, Phe 1.02, His 0.99.

Melting point: 175° to 178° C.; $[\alpha]_D^{22} = -68.0°$ (c=0.1, 0.01M AcOH).

EXAMPLE 2

Preparation of Trp$^7$, Gln$^8$-gonadoliberin M: 1226

(a) Synthesis 2.5 g (1 mmole) of benzhydrylamine resin.HCl (0.4 meq/g) are swollen in $CH_2Cl_2$, then 3.62 g of Glp—His(DNP)—Trp—Ser(OBzl)—Tyr—Gly—Trp—Gln—Pro—Gly—peptide resin are prepared according to Example 1/a.

ΔW: 1.12 g (76%) ($M_{protected\ peptide}$: 1468).

(b) Deprotection and cleavage of the peptide from the resin

Cleavage of the DNP group

The protected decapeptide resin (3.62 g) is stirred in 20 ml of DMF and 1 ml of propylamine for 60 min, at room temperature, then the partially protected peptide resin is filtered off, washed with $CH_2Cl_2$ and ethanol, finally it is dried in vacuo.

HF cleavage

After removing the DNP-protecting group the peptide is treated by HF according to Example 1/b. In this way 0.8 g (65%) of crude decapeptide amide are gained.

(c) Gel filtration

The gel filtration is carried out according to Example 1/c. Yield: 520 mg (42%).

(d) Preparative HPLC

The process is carried out according to Example 1/d, with the exception that the LRP-1 gel is equilibrated with a solution of 18% methanol in 30% acetic acid. The crude, gel-filtered material is eluted from the column with a linear gradient system of methanol-—30% acetic acid (18–35% methanol). Thus 380 mg (31%) of the pure peptide are obtained.

$R_f^1 = 0.66$; $R_f^5 = 0.57$; $R_f^8 = 0.78$.

Amino acid analysis: Ser 0.93, Glu 1.93, Pro 1.00, Gly 2.04, Tyr 0.98, Trp 1.86, His 1.03.

EXAMPLE 3

Preparation of Trp$^7$, Leu$^8$, desGly$^{10}$-gonadoliberin ethylamide M: 1198

(a) Synthesis

At first Boc-Pro-resin is prepared according to the method of Merrifield [Merrifield, R. B., J. Am. Chem. Soc. 86, 304 (1964)]. 2.0 g (1 mmole) of Boc-Pro-resin (0.5 meq/g) are swollen for two hours, then the appropriate amino acids are coupled to the resin one after the other according to Example 1/a. After the last cycle 3.02 g of Glp—His(DNP)—Trp—Ser(OBzl)—Tyr(OBzl)—Gly—Trp—Leu—Pro—nonapeptide resin are gained.

ΔW: 1.02 g (83%) ($M_{protected\ peptide}$: 1486).

(b) Deprotection and cleavage of the peptide from the resin

First the DNP protecting group is removed in compliance with Example 2/b. Then the partially protected peptide is split off from the resin as its ethylamide form [Coy, D. H. et al., Biochemistry 13, 323–326 (1974)]. For this purpose the peptide resin is stirred with 15 ml of conducted ethylamine at 0° C. for 3 hours. The excess of the ethylamine is eliminated in nitrogen gas stream. The residue is washed with ethanol and DMF, then filtered. The filtrate is evaporated in vacuo, the residue is treated with ether and the solid material is filtered.

Complete deprotection of the peptide is carried out by a treatment with anhydrous HF according to Example 1/b. Yield: 710 mg (59%).

(c) Gel filtration

The nonapeptide ethylamide is led through a Sephadex G-25 column in 30% acetic acid according to Example 1/c. Yield: 490 mg (41%).

(d) Silica gel chromatography

The crude peptide is purified on a column of Kieselgel 60, 2×100 cm (230–400 mesh, Merck) in a 30:20:6:11 mixture of ethyl acetate, pyridine, acetic acid, water at a flow rate of 8 ml/h. 4 ml fractions are collected and the elution is monitored by TLC. The fractions containing the pure substance are evaporated and lyophilized. Yield: 320 mg (26%).

$R_f^1 = 0.61$; $R_f^2 = 0.42$; $R_f^8 = 0.75$.

Amino acid analysis: Ser 0.89, Glu 0.96, Pro 0.95, Gly 0.97, Leu 1.00, Tyr 1.02, Trp 1.88, His 1.03.

EXAMPLE 4

Preparation of Phe$^7$, Gln$^8$-gonadoliberin M: 1187

(a) Synthesis 1.25 g (1 mmole) of benzhydrylamine.HCl resin (0.8 meq/g) are swollen in $CH_2Cl_2$ for two hours, then according to Example 1/a 2.9 g of Glp—His(Tos)—Trp—Ser(OBzl)—Tyr(OBzl)—Gly—Phe—Gln—Pro—Gly—peptide resin are prepared.

ΔW: 1.27 g (83%) ($M_{protected\ peptide}$: 1521).

(b) HF cleavage

The protected peptide is treated with anhydrous HF according to Example 1/b. Thus 980 mg (82%) of deprotected material are obtained.

(c) Gel filtration

The crude decapeptide amide is purified on a column of Sephadex G-25 in 2M acetic acid, according to Example 1/c. Yield: 576 mg (49%).

(d) Preparative HPLC

The process is carried out according to Example 1/d, with the exception that the LRP-1 gel is equilibrated with a solution of 10% methanol in 20% acetic acid. The elution is carried out with a linear gradient system of methanol--20% acetic acid (10-25% methanol, 150-150 ml), then it is continued with a 25-40% methanol-containing linear gradient system (150-150 ml of each). Fractions containing the pure peptide are collected and evaporated. Yield: 448 mg, (38%).

$R_f^1 = 0.12$, $R_f^5 = 0.7$, $R_f^6 = 0.24$, $R_f^7 = 0.87$.

Amino acid analysis: Ser 0.87, Glu 2.05, Pro 1.03, Gly 2.13, Tyr 0.92, Phe 1.00, His 0.95, Trp 0.81.

Melting point: 182° C.

EXAMPLE 5

Preparation of Phe⁷, Leu⁸-gonadoliberin M: 1172

(a) Synthesis 0.62 g (0.5 mmole) of benzhydrylamine.HCl resin (0.8 meq/g) is swollen in $CH_2Cl_2$ for two hours, then according to Example 1/a 1.33 g of Glp—His(Tos)—Trp—Ser(OBzl)—Tyr(OBzl)—Gly—Phe—Leu—Pro—Gly—peptide resin are synthetized.

ΔW: 695 mg (92%) ($M_{protected\ peptide}$: 1506).

(b) HF cleavage

The protected peptide is treated by HF according to Example 1/b. Thus 510 mg (87%) of the crude decapeptide are obtained.

(c) Gel filtration

The crude decapeptide amide obtained in step (b) is loaded on a column of Sephadex G-25 in 2M acetic acid and is purified according to Example 1/c. Yield: 363 mg (62%).

(d) Silica gel chromatography

The peptide is further purified on a column of Kieselgel 60 (2×100 cm) in a 1:1:1:1 mixture of n-butanol, acetic acid, water and ethyl acetate. The contents of the fractions are monitored at 280 nm and by TLC. Thus 299 mg (51%) of the pure decapeptide amide are obtained.

$R_f^1 = 0.55$; $R_f^2 = 0.39$; $R_f^5 = 0.62$; $R_f^7 = 0.73$.

Amino acid analysis: Ser 0.91, Glu 0.97, Pro 1.07, Gly 2.12, Leu 1.00, Tyr 1.03, Phe 0.94, His 1.05.

EXAMPLE 6

Preparation of D—Phe⁶, Gln⁸, desGly¹⁰ gonadoliberin ethylamide M: 1198

(a) Boc—His(DNP)—Trp—OMe M: 623

21.12 g (50 mmoles) of Boc—His(DNP)—OH are dissovled in 100 ml of DMF and the solution is cooled to 0° C. Thereafter 10.32 g (50 mmoles) of DCCI and 7.66 g (50 mmoles) of N-hydroxy-benztriazole are added under stirring. The mixture is stirred at 0° C. for 10 minutes and the precipitated dicyclohexyl-urea is filtered off.

12.74 g (50 mmoles) of H—Trp—OMe.HCl are dissolved in 70 ml of DMF and the solution is cooled to 0° C. 693 ml (50 mmoles) of triethylamine are added and after stirring for 5 minutes the precipitated triethyl amine hydrochloride is filtered off.

The two solutions are combined and stirred at 0° C. overnight. Thereafter the precipitated DCU is filtered off and the solution is evaporated to dryness. The oily residue is dissolved in 500 ml of ethyl acetate and shaken with three 100-ml portions of ice-cold 1M $KHSO_4$ solution, five 100-ml portions of a saturated $NaHCO_3$ solution and finally with two 100-ml portions of a 10% NaCl solution. The organic phase is dried over magnesium sulfate, filtered and evaporated to dryness. The obtained oily substance is powdered with petroleum ether, filtered and dried. The crystalline product obtained can be recrystallized from ethyl acetate with petroleum ether. Yield: 27.7 g (89%).

Melting point: 119° to 122° C.; $[\alpha]_D^{22} = +14.1°$ (c=1, DMF).

$R_f^4 = 0.62$.

(b) H—His(DNP)—Trp—OMe.2HCl M: 522.5 (free base); 595 (0.2HCl)

24.9 g (40 mmoles) of Boc—His(DNP)—OMe dipeptide are dissolved in 100 ml of methanol, and 100 ml of a 4n methanolic hydrochloric acid solution are added. The mixture is allowed to stand 30 minutes at room temperature, while the dipeptide hydrochloride is crystallized. The crystals are filtered off, washed with ether and dried. Yield: 21.91 g (92%).

Melting point: 198° to 202° C.; $[\alpha]_D^{22} = 0.49°$ (c=1, DMF).

$R_f^3 = 0.46$, $R_f^4 = 0.18$.

(c) Glp—His(DNP)—Trp—OMe M: 634

4.85 g (36.8 mmoles) of L-pyroglutamic acid, 7.58 g of dicyclohexyl-carbodiimide and 5.63 g of N-hydroxybenztriazole are dissolved in 100 ml of DMF. The mixture is stirred at 5° to 10° C. for 10 minutes whereupon the precipitated DCU is filtered off.

20.84 g (35 mmoles) of H—His(DNP)—Trp—OMe.2HCl are dissolved in 100 ml of dimethyl formamide, and 9.72 ml (70 mmoles) of triethylamine are added to the solution. After stirring for 5 minutes the precipitated triethylamine hydrochloride is filtered off. The two solutions are combined and stirred at room temperature overnight. Then 90 ml of acetone are added to the mixture and the precipitated insoluble material is filtered off. Evaporation of the solution affords an oily material, which is triturated with ethyl acetate, filtered and dried. The dry crystalline material is washed with three 25 ml portions of water and dried. The product can be recrystallized by dissolving in hot ethyl acetate and cooling. Yield 18.42 g (83.1%).

Melting point: 148° to 151° C.; $[\alpha]_D^{23} = +5.2$ (c=1, DMF).

$R_f^3 = 0.53$, $R_f^4 = 0.38$.

(d) Glp—His—Trp—OMe M: 466

15.84 g (25 mmoles) of Glp—His(DNP)—Trp—OMe protected tripeptide are dissolved in a mixture of 100 ml of DMF and 40 ml of water. 4 ml of mercapto-ethanol are added and the pH of the solution is adjusted to 8 with triethylamine. It is allowed to stand at room temperature for 30 minutes, and is evaporated to dryness in vacuo. The oily material is triturated with ether, filtered and dried. The product obtained is dissolved in a small portion of methanol and recrystallized by adding ether.

The precipitated crystals are filtered off and dried. Yield: 10.92 g (93.6%).

Melting point: 228° to 232° C.; $[\alpha]_D^{22} = +4.04°$ (c=0.42, DMF).

$R_f^2 = 0.30$.

(e) Glp—His—Trp—N₂H₃ M: 466.5

9.33 g (20 mmoles) of Glp—His—Trp—OMe tripeptide are dissolved in 250 ml of methanol. 20 ml of 98% hydrazine hydrate are added to the solution. The reaction mixture is stirred at 40° C. for 3 hours and subsequently at room temperature overnight. The precipitated material is then filtered off, washed with cold methanol and dried. Yield: 7.58 g (81.2%).

Melting point: 166° to 169° C.; $[\alpha]_D^{22} = -22.3$ (c=0.5, DMF).

$R_f^1 = 0.50$, $R_f^2 = 0.14$.

(f) Glp—His—Trp—Ser—Tyr—OMe M: 717

7.0 g (15 mmoles) of Glp—His—Trp—N₂H₃ obtained in step (e) are dissolved in 60 ml of DMF. The solution is cooled to 0° C. and 7.5 ml (45 mmoles) of a 6n HCl solution are added under stirring. Thereafter 1.035 g (15 mmoles) of NaNO₂ are added dropwise to the mixture as a concentrated aqueous solution, and the mixture is stirred at 0° C. for further 15 minutes. A solution of 4.78 g (15 mmoles) of H—Ser—Tyr—OMe.HCl in 15 ml of DMF are added to the reaction mixture. The pH is adjusted to neutral with 6.25 ml (45 mmoles) of triethylamine and the mixture is stirred at 0° to 4° C. overnight. The next day it is evaporated to dryness in vacuo and the oily product is triturated with ether.

12.1 g (100%) of the aimed compound containing a small amount of impurity are obtained. This product can be converted into hydrazide without purification and the hydrazide obtained can be readily crystallized.

Physical properties of a control sample recrystallized from methanol:

melting point: 188° to 190° C.; $[\alpha]_D^{22} = -3.48°$ (c=1, DMF).

$R_f^1 = 0.58$, $R_f^2 = 0.26$.

(g) Glp—His—Trp—Ser—Tyr—N₂H₃ M: 717

12 g of crude, powdered Glp—His—Trp—Ser—Tyr—OMe pentapeptide ester are dissolved in 200 ml of methanol, and 10 ml of 98% hydrazine hydrate are added. The mixture is stirred at 40° C. for 3 hours, then stirred at room temperature overnight, whereupon the precipitated crystals are filtered off and dried in an exsiccator over concentrated sulfuric acid. The dry crystalline material is dissolved in 250 ml of a 0.5n hydrochloric acid solution. The pH of the solution is adjusted to 8 with saturated sodium carbonate solution. After standing at 0° C. for 2 hours the precipitated crystals are filtered, washed with ice-cold water and dried. Yield: 6.12 g (56.9%, calculated for the two steps).

Melting point: 205° to 206° C.; $[\alpha]_D^{22} = -21.51°$ (c=1, DMF).

$R_f^1 = 0.39$, $R_f^2 = 0.14$.

Hydrazine nitrogen: found: 3.79%, 3.76% calculated: 3.91%.

(h) Z—Gln—Pro—NHEt M: 405

3.242 g of proline ethylamide (obtained from 22.8 mmoles of Z—Pro—NHEt by hydrogenolysis) are dissolved in 70 ml of tetrahydrofurane (THF), then 5.6 g (20 mmoles) of Z—Gln—OH and 1.034 g of N-hydroxy-benztriazole are added to the solution. The reaction mixture is cooled to 0° C. and the solution of 5.34 g (25.9 mmoles) of dicyclohexyl-carbodiimide in THF is dropped to the stirred reaction mixture. Stirring is continued for 5 hours at 0° C., then for 20 hours at room temperature. The precipitate is filtered, washed with THF, then the filtrate is evaporated in vacuo and the residue is dissolved in chloroform. The solution is shaken with three 35 ml portions of a mixture of NH₄OH and water (1:5), two 20 ml portions of water, three 35 ml portions of 0.1n HCl solution and finally two 20 ml portions of water. The organic phase is dried over anhydrous sodium sulfate, filtered, washed with chloroform and evaporated. The obtained oily residue is dissolved in a mixture of 35 ml of THF and 50 ml of ethyl acetate, then filtered. The solution is evaporated and the residue is triturated with ether. The obtained solid product is filtered, washed with ether and dried in vacuo. Yield: 7.68 g (95%).

$R_f^1 = 0.73$, $R_f^6 = 0.45$.

(i) Z—Leu—Gln—Pro—NHEt M: 518.6

4.5 g (11 mmoles) of Z—Gln—Pro—NHEt are dissolved in 30 ml of glacial acetic acid and 55 ml of 4n hydrogen bromide in glacial acetic acid are added to the solution. The reaction mixture is kept for 90 minutes at room temperature, then 250 ml of anhydrous ether are added to the mixture and it is kept for 60 minutes at room temperature. The supernatant is decanted, 100 ml of ether are added to the residue and after 15 minutes it is filtered and washed with ether. The solid residue is dried in vacuo over phosphorus pentoxide and sodium hydroxide. Yield: 4.9 g (hygroscopic).

3.8 g (11 mmoles) of the obtained dipeptide ethylamide.HBr are suspended in 150 ml of chloroform, and 7 ml of triethylamine are added to the suspension. 6.4 g of carbobenzoxy-leucyl-pentachlorophenylester in 65 ml of chloroform are added. The reaction mixture is stirred overnight at room temperature. The next day it is washed with 1n hydrochloric acid, saturated sodium chloride, 2n ammonium-hydroxide and repeatedly with saturated sodium-chloride solution. The chloroform phase is dried over anhydrous sodium sulfate and evaporated in vacuo. The residue is triturated with ether, filtered, washed with ether and dried in vacuo. Yield: 4.6 g (81%).

(j) H—Leu—Gln—Pro—NHEt.HBr M: 465.5

The crude product prepared in step (i) is dissolved in 10 ml of glacial acetic acid and stirred for 60 minutes at room temperature, then the solution is diluted with 100 ml of anhydrous ether. The precipitate is filtered and dried in vacuo. Yield: 3.54 g (76%).

$R_f^1 = 0.1$, $R_f^5 = 0.55$, $R_f^6 = 0.13$, $R_f^8 = 0.77$.

Amino acid analysis: Glu 1.05, Pro 1.19, Leu 1.00.

(k) Boc—D—Phe—Leu—Gln—Pro—NHEt M: 631.7

2.33 g (5 mmoles) of H—Leu—Gln—Pro—NHEt.HBr are dissolved in 5 ml of DMF and cooled to 0° C., then 0.7 ml (5 mmoles) of triethylamine and 2.57 g (5 mmoles) of tert.-butyloxycarbonyl-D-phenylalanyl-pentachlorophenylester in 10 ml of DMF are added to the solution. The pH is adjusted to a value between 7 and 8, then the reaction mixture is stirred for 48 hours at room temperature, meanwhile the pH-value is adjusted from time to time to neutral with triethylamine. After evaporating the reaction mixture the remaining substance is triturated with ether, then filtered and dried.

The obtained crude product is subjected to deprotection without further purification. Yield: 2.81 g (89%).

(l) H—D—Phe—Leu—Gln—Pro—NHEt.TFA M: 645.6

1.26 g (2 mmoles) of Boc—D—Phe—Leu—Gln—Pro—NHEt are dissolved in 10 ml of trifluoro-acetic acid and stirred for 20 minutes at room temperature. The trifluoro-acetic acid is evaporated in vacuo and the residue is triturated with ether, filtered and dried. The residue is submitted to chromatography on a silica gel column with a 4:1:1 mixture of n-butanol, acetic acid and water. The appropriated fractions are collected and evaporated to vacuo. The residue is dissolved in a few ml of water, then lyophilized.

Yield: 880 mg (68%).
$R_f^2 = 0.25$, $R_f^6 = 0.35$.
Melting point: 142° C.; $[\alpha]_D^{20} = -66°$ (c=0.1, DMF).

(m) Glp—His—Trp—Ser—Tyr—D—Phe—Leu—Gln—Pro—NHEt M: 1199

286 mg (0.4 mmole) of the pentapeptide hydrazide Glp—His—Trp—Ser—Tyr—N$_2$H$_3$ prepared in step (g) are dissolved in 10 ml of dimethyl formamide. The solution is cooled to −10° C., then under stirring 0.27 ml of 6n hydrochloric acid and thereafter a concentrated aqueous solution of 30.2 mg of sodium nitrite are added dropwise. After 5 minutes the solution of the trifluoro-acetate salt of 258 mg (0.4 mmole) of the tetrapeptide H—D—Phe—Leu—Gln—Pro—NHEt prepared in 1 ml of dimethyl formamide with 0.27 ml of triethylamine at −10° C. is added. If necessary, the reaction mixture is adjusted to a neutral pH-value with triethylamine, then it is stirred for 1 hour at a temperature of −5° C., for 1 hour at 0° C. and for 12 hours at room temperature.

The dimethyl formamide is eliminated in vacuo, the oily residue is dissolved in 5 ml of 0.2n acetic acid and the solution is submitted to chromatography on a Sephadex G-25 column (2×95 cm) with 0.2n acetic acid. The appropriate fractions are collected and lyophilized. Yield: 298 mg (62%).

$R_f^1 = 0.39$, $R_f^2 = 0.13$, $R_f^5 = 0.48$, $R_f^6 = 0.14$.
Amino acid analysis: Ser 0.89, Glu 1.98, Pro 0.97, Leu 1.00, Tyr 1.03, Phe 0.99, His 1.01, Trp 0.91.

EXAMPLE 7

Preparation of Trp$^7$, Gln$^8$, desGly$^{10}$-gonadoliberin ethylamide M: 1220

(a) Boc—Gln—Pro—NHEt M: 370

1.0 g (7 mmoles) of proline ethylamide are dissolved in 15 ml of dimethyl formamide and the pH-value is adjusted to 8 with triethylamine, then 3.2 g (8.4 mmoles) of tert.-butyloxy-carbonyl-glutaminyl-p-nitro-phenylester in 15 ml of dimethyl formamide are added to the solution. The reaction mixture is stirred for 48 hours at room temperature, while the pH-value is adjusted from time to time to 8 with triethylamine. After evaporating the reaction mixture the oily residue is dissolved in water, washed with ether and the separated aqueous phase is evaporated in vacuo and dried. Yield: 1.93 g (74.5%).

$R_f^3 = 0.76$.

(b) H—Gln—Pro—NHEt.TFA M: 270 (free base); M: 367 (TFA salt)

1.9 g (7.2 mmoles) of Boc—Gln—Pro—NHEt are dissolved in 10 ml of trifluoro-acetic acid and stirred for 20 minutes at room temperature. The solution is evaporated in vacuo, the residue is triturated with ether, filtered and dried in vacuo. Yield: 1.52 g (58%).

$R_f^1 = 0.45$, $R_f^7 = 0.45$, $R_f^9 = 0.25$, $R_f^{10} = 0.30$.
Hygroscopic substance; $[\alpha]_D^{20} = -34.8°$ (c=1, MeOH).

(c) Boc—Trp—Gln—Pro—NHEt M: 557

500 mg (1.85 mmoles) of H—Gln—Pro—NHEt are dissolved in 10 ml of dimethyl formamide. The pH-value is adjusted to 8 with triethylamine, then 608 mg (2 mmoles) of tert.butyloxy-carbonyl-tryptophane in 10 ml of dimethyl formamide and 620 μl (4 mmoles) of N,N'-diisopropyl carbodiimide are added. The reaction mixture is stirred for 48 hours at room temperature, then evaporated in vacuo. The residue is dissolved in ethyl acetate and diluted with ether. The precipitated Boc—Trp—Gln—Pro—NHEt is filtered, washed with ether and dried. Yield: 740 mg (72%).

$R_f^2 = 0.75$, $R_f^3 = 0.38$.

(d) H—Trp—Gln—Pro—NHEt.TFA M: 456.5 (free base); M: 554 (TFA salt)

700 mg (1.25 mmoles) of Boc—Trp—Gln—Pro—NHEt are dissolved in 15 ml of a 1:1 mixture of trifluoro-acetic acid and CH$_2$Cl$_2$ and stirred for 20 minutes at room temperature. Then the solution is evaporated in vacuo and the residue is triturated with ether. The solid residue is filtered and dried. The thus-obtained crude product of about 500 mg is purified by chromatography on a silica gel column in a 47:20:6:11 mixture of ethyl acetate, pyridine, acetic acid and water. The appropriate fractions are collected, evaporated to dryness in vacuo and the residue is triturated with ether. Thus 360 mg (52%) of a white powder are obtained.

$R_f^1 = 0.46$, $R_f^2 = 0.18$.
Melting point: 119° to 123° C.; $[\alpha]_D^{20} = -4.8°$ (c=0.1, 0.1n HCl).

(e) Boc—Gly—Trp—Gln—Pro—NHEt M: 613.7

350 mg (0.76 mmole) of H—Trp—Gln—Pro—NHEt are dissolved in dimethyl formamide and coupled with 104 mg (0.8 mmole) of Boc—Gly according to step (c) of Example 7. Thus 375 mg (81%) of a crystalline substance are obtained.

$R_f^3 = 0.88$, $R_f^5 = 0.82$, $R_f^6 = 0.61$.

(f) H—Gly—Trp—Gln—Pro—NHEt.TFA M: 609.6

375 mg (0.6 mmole) of Boc—Gly—Trp—Gln—Pro—NHEt are deprotected and purified according to step (d) of Example 7. Thus 285 mg (76.6%) of a white powder are obtained.

$R_f^2 = 0.08$, $R_f^3 = 0.16$, $R_f^5 = 0.67$, $R_f^6 = 0.28$.

(g) Glp—His—Trp—Ser—Tyr—Gly—Trp—Gln—Pro—NHEt M: 1216.4

286 mg (0.4 mmole) of the pentapeptide hydrazide Glp—His—Trp—Ser—Tyr—N$_2$H$_3$ are coupled with 243.8 mg (0.4 mmole) of H—Gly—Trp—Gln—Pro—NHEt.TFA obtained according to step (m) of Example 6. Thus 252.9 mg (52%) of a pure substance are obtained.

$R_f^1=0.26$, $R_f^5=0.32$.

Amino acid analysis: Ser 0.87, Glu 2.02, Pro 0.91, Gly 1.00, Tyr 1.12, His 1.05, Trp 1.80.

EXAMPLE 8

Preparation of injections for intramuscular, subcutaneous or intravenous administration (a) The gonadoliberin derivative of the formula (I) is dissolved in distilled water, a physiological saline solution or buffered aqueous solution, in a concentration of 1 to 10 mg/ml. The solution is filtered to sterile, small portions containing 50–500 μg of the active ingredient which are filled into ampoules and lyophilized, then the ampoules are sealed. The active ingredient content of the ampoules is freshly dissolved before treatment by adding 1–10 ml of distilled water, and a volume corresponding to the desired dose is administered.

(b) 20–500 μg/ml. of a gonadoliberin derivative of the formula (I) are dissolved in an aqueous solution containing 0.9% of NaCl and 0.9% of benzyl alcohol. The portions containing 20–500 μg/ml active ingredient are filled into ampoules which are then sealed. The solutions obtained can directly be injected.

What we claim is:

1. Gonadoliberin derivatives of the general formula (I)

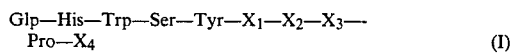

wherein
$X_1$ is a glycyl, D—Phe, D—Ser, D—Trp or D—Ala group,
$X_2$ is L-leucyl, L-phenylalanyl or L-tryptophyl group,
$X_3$ is L-glutaminyl, L-asparaginyl or L-leucyl group, and
$X_4$ is a glycylamide or ethylamide group,
with the proviso that if $X_2$ is an L-tryptophyl group then $X_3$ may stand only for L-glutaminyl or L-asparaginyl group, and the addition salts formed with therapeutically usable acids and complexes thereof.

2. A compound selected from the group consisting of

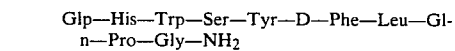

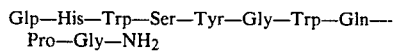

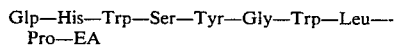

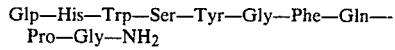

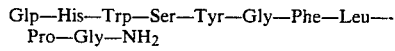

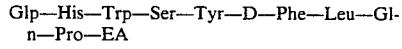

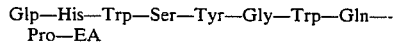

and the therapeutically usable salts and complexes thereof.

3. A pharmaceutical composition which is effectively usable for the reproduction process of fish, birds and mammals comprising as active ingredient at least one compound of the general formula (I), wherein $X_1$, $X_2$, $X_3$ and $X_4$ are as defined in claim 1, or a pharmaceutically acceptable salt or complex thereof, together with a carrier or diluent.

4. A process for the preparation of a pharmaceutical composition, characterized in that a compound of the general formula (I), wherein $X_1$, $X_2$, $X_3$ and $X_4$ are as defined in claim 1, or a pharmaceutically acceptable salt or complex thereof is admixed with a conventional pharmaceutical carrier or diluent.

* * * * *